United States Patent
Hyeon et al.

(10) Patent No.: US 11,419,534 B2
(45) Date of Patent: Aug. 23, 2022

(54) CORE-SHELL NANOWIRE, METHOD OF FORMING CORE-SHELL NANOWIRE, AND STRETCHABLE COMPOSITE COMPRISING CORE-SHELL NANOWIRE

(71) Applicants: Seoul National University R&DB Foundation, Seoul (KR); INSTITUTE FOR BASIC SCIENCE, Daejeon (KR)

(72) Inventors: Taeghwan Hyeon, Seoul (KR); Daehyeong Kim, Seoul (KR); Sangihn Han, Seoul (KR); Suji Choi, Seoul (KR); Dongjun Jung, Seoul (KR)

(73) Assignees: Seoul National University R&DB Foundation, Seoul (KR); INSTITUTE FOR BASIC SCIENCE, Daejeon (KR)

( * ) Notice: Subject to any disclaimer, the term of this patent is extended or adjusted under 35 U.S.C. 154(b) by 182 days.

(21) Appl. No.: 16/759,277

(22) PCT Filed: Oct. 25, 2018

(86) PCT No.: PCT/KR2018/012692
§ 371 (c)(1),
(2) Date: Apr. 24, 2020

(87) PCT Pub. No.: WO2019/083294
PCT Pub. Date: May 2, 2019

(65) Prior Publication Data
US 2020/0315479 A1    Oct. 8, 2020

(30) Foreign Application Priority Data
Oct. 27, 2017  (KR) .......................... 10-2017-0141326

(51) Int. Cl.
*A61B 5/283*    (2021.01)
*A61N 1/05*     (2006.01)
(Continued)

(52) U.S. Cl.
CPC ............ *A61B 5/283* (2021.01); *A61N 1/0597* (2013.01); *B22F 1/07* (2022.01); *B22F 9/20* (2013.01);
(Continued)

(58) Field of Classification Search
None
See application file for complete search history.

(56) References Cited

U.S. PATENT DOCUMENTS 9,491,853 B2 *   11/2016  Gaynor ................. G03F 7/0047
2011/0014256 A1 *  1/2011  Chang .................... A01N 59/16
                                                                424/405
(Continued)

FOREIGN PATENT DOCUMENTS

JP      2016535649 A    11/2016
KR    20120061305 A     6/2012
(Continued)

OTHER PUBLICATIONS

Moon et al. "Ag/Au/Polypyrrole Core-shell Nanowire Network for Transparent, Stretchable and Flexible Supercapacitor in Wearable Energy Devices," Scientific Reports 7:41981, published Feb. 3, 2017, accessible online from www.nature.com/scientificreports; PDF pp. 1-10 are attached (Year: 2017).*
(Continued)

*Primary Examiner* — Katie L. Hammer

(57) ABSTRACT

A core-shell nanowire, a method of forming the core-shell nanowire and a stretchable composite comprising the core-shell nanowire are provided. The core-shell nanowire comprises a core comprising a conductive metal and a shell comprising a biocompatible metal. The method of forming the core-shell nanowire comprises a step of forming a core-shell nanowire by carrying out epitaxial growth of a biocompatible metal on a surface of a core comprising a
(Continued)

conductive metal. The stretchable composite comprises a first core-shell nanowire/polymer composite comprising first core-shell nanowires and a first polymer, a first insulating layer disposed on the first core-shell nanowire/polymer composite, and a second core-shell nanowire/polymer composite disposed on the first insulating layer and comprising second core-shell nanowires and a second polymer.

6 Claims, 17 Drawing Sheets

(51) Int. Cl.
| | | |
|---|---|---|
| H01B 1/22 | (2006.01) | |
| H01B 5/14 | (2006.01) | |
| H01B 13/00 | (2006.01) | |
| B22F 1/07 | (2022.01) | |
| B32B 5/02 | (2006.01) | |
| B32B 5/26 | (2006.01) | |
| C30B 29/60 | (2006.01) | |
| B32B 15/01 | (2006.01) | |
| B22F 9/20 | (2006.01) | |
| B22F 1/102 | (2022.01) | |
| B22F 1/054 | (2022.01) | |
| B22F 1/17 | (2022.01) | |
| H01B 7/06 | (2006.01) | |
| A61B 5/25 | (2021.01) | |
| B22F 9/24 | (2006.01) | |

(52) U.S. Cl.
CPC ............... *B32B 5/028* (2013.01); *B32B 5/26* (2013.01); *B32B 15/018* (2013.01); *C30B 29/60* (2013.01); *H01B 1/22* (2013.01); *H01B 5/14* (2013.01); *H01B 13/0036* (2013.01); *A61B 5/25* (2021.01); *A61B 2562/0215* (2017.08); *A61B 2562/12* (2013.01); *B22F 1/0547* (2022.01); *B22F 1/102* (2022.01); *B22F 1/17* (2022.01); *B22F 9/24* (2013.01); *B22F 2301/255* (2013.01); *H01B 7/06* (2013.01)

(56) References Cited

U.S. PATENT DOCUMENTS

| | | | |
|---|---|---|---|
| 2011/0278058 A1* | 11/2011 | Sundararaj | H05K 9/009 977/932 |
| 2013/0041235 A1* | 2/2013 | Rogers | A61B 5/1107 600/306 |
| 2015/0014022 A1* | 1/2015 | Young | H05K 1/0313 174/251 |
| 2015/0380355 A1* | 12/2015 | Rogers | H01L 23/5387 257/773 |
| 2018/0146545 A1* | 5/2018 | Wang | C08F 297/046 |
| 2020/0392654 A1* | 12/2020 | Fowler | H01B 1/20 |

FOREIGN PATENT DOCUMENTS

| | | |
|---|---|---|
| KR | 20130045843 A | 5/2013 |
| KR | 101503391 B1 | 3/2015 |
| KR | 101688739 B1 | 12/2016 |
| KR | 20160144069 A | 12/2016 |
| WO | WO2011100059 A1 | 8/2011 |
| WO | WO2015051085 A2 | 4/2015 |

OTHER PUBLICATIONS

Kwon et al., "Highly stretchable, printable nanowire array optical polarizers", Royal Society of Chemistry, Nanoscale, 2016.
Internal Search Report dated Feb. 11, 2019 for PCT application No. PCT/KR2018/012692.

* cited by examiner

CORE-SHELL NANOWIRE, METHOD OF FORMING CORE-SHELL NANOWIRE, AND STRETCHABLE COMPOSITE COMPRISING CORE-SHELL NANOWIRE

CROSS-REFERENCE TO RELATED APPLICATION

This application is a national stage application, filed under 35 U.S.C. § 371, of International Patent Application No. PCT/KR2018/012692, filed on Oct. 25, 2018, which claims benefit of Korean application No. 10-2017-0141326, filed on Oct. 27, 2017, the contents of which are incorporated by reference.

TECHNICAL FIELD

The present invention relates to a core-shell nanowire, a method of forming the core-shell nanowire and a stretchable composite comprising the core-shell nanowire are provided.

BACKGROUND ART

The heart is one of the most important organs that are activated by propagation of electrical conduction through the His-Purkinje conduction system. Monitoring electrical activities of the heart helps to give a doctor an insight into the heart condition to diagnose specific diseases which is determined by a waveform of action potential in clinical care. In particular, local activation maps provide the information of the location of the impaired myocardium, and thus multiple spatially distributed recordings are demanded for interpreting comprehensive heart diseases. The conventional anatomical approach of the catheter electrode through the blood vessels makes electrical pacing at the desired site of the heart difficult. In order to solve these problems, an electrode with a net shape has been studied, but there is a problem that this electrode release highly toxic metal components.

DISCLOSURE

Technical Problem

In order to solve the above mentioned problems, the present invention provides a core-shell nanowire having good biocompatibility.

The present invention provides a method of forming the core-shell nanowire.

The present invention provides a stretchable composite comprising the core-shell nanowire.

The other objects of the present invention will be clearly understood with reference to the following detailed description and the accompanying drawings.

Technical Solution

A core-shell nanowire according to embodiments of the present invention comprises a core comprising a conductive metal and a shell comprising a biocompatible metal.

A method of forming a core-shell nanowire according to embodiments of the present invention comprises a step of forming a core-shell nanowire by carrying out epitaxial growth of a biocompatible metal on a surface of a core comprising a conductive metal.

A stretchable composite according to embodiments of the present invention comprises a first core-shell nanowire/polymer composite comprising first core-shell nanowires and a first polymer, a first insulating layer disposed on the first core-shell nanowire/polymer composite, and a second core-shell nanowire/polymer composite disposed on the first insulating layer and comprising second core-shell nanowires and a second polymer.

Advantageous Effects

A core-shell nanowire according to embodiments of the present invention can have good biocompatibility. The stretchable composite comprising the core-shell nanowire can have high conductivity and good biocompatibility. The stretchable composite can be used in various fields such as a medical device and the like.

BEST MODE

Figure 1:
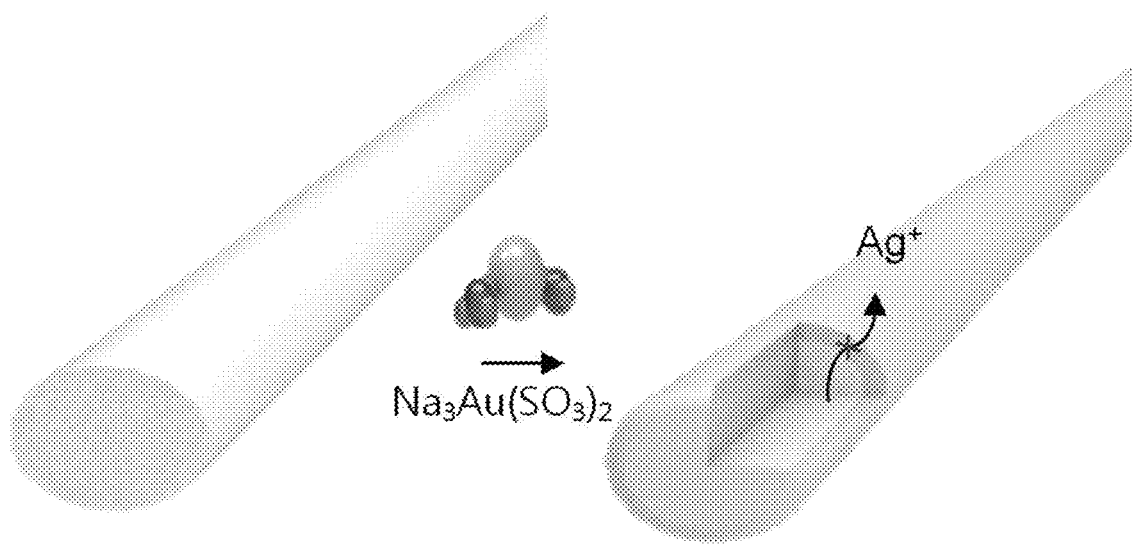
FIG. 1 schematically shows a process for forming a gold shell on a silver nanowire without a galvanic reaction according to one embodiment of the present invention.

Hereinafter, a detailed description will be given of the present invention with reference to the following embodiments. The purposes, features, and advantages of the present invention will be easily understood through the following embodiments. The present invention is not limited to such embodiments, but may be modified in other forms. The embodiments to be described below are nothing but the ones provided to bring the disclosure of the present invention to perfection and assist those skilled in the art to completely understand the present invention. Therefore, the following embodiments are not to be construed as limiting the present invention.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. It will be understood that when an element is referred to as being "on" another element, it can be directly on the other element or intervening elements may be present therebetween.

The size of the element or the relative sizes between elements in the drawings may be shown to be exaggerated for more clear understanding of the present invention. In addition, the shape of the elements shown in the drawings may be somewhat changed by variation of the manufacturing process or the like. Accordingly, the embodiments disclosed herein are not to be limited to the shapes shown in the drawings unless otherwise stated, and it is to be understood to include a certain amount of variation.

The term Ag@Au used herein represents a core-shell structure where Ag before @ represents a core and Au after @ represents a shell. Ag NW means a silver nanowire and Ag@Au NW means an Ag@Au nanowire. In addition, a core-shell nanowire/polymer composite means a composite formed by mixing core-shell nanowires and a polymer. For example, Ag@Au NW/SBS means a composite formed by mixing Ag@Au nanowires and SBS (styrene-butadiene-styrene) rubber. A core-shell nanowire according to embodiments of the present invention comprises a core comprising a conductive metal and a shell comprising a biocompatible metal.

The conductive metal may comprise silver and the biocompatible metal may comprise gold.

A method of forming a core-shell nanowire according to embodiments of the present invention comprises a step of forming a core-shell nanowire by carrying out epitaxial growth of a biocompatible metal on a surface of a core comprising a conductive metal.

The epitaxial growth may be carried out by a gold sulfite complex. Galvanic reaction between the conductive metal and the biocompatible metal may be inhibited by the gold sulfite complex. The conductive metal may comprise silver, the biocompatible metal may comprise gold, and the gold sulfite complex may comprise $Na_3Au(SO_3)_2$.

A stretchable composite according to embodiments of the present invention comprises a first core-shell nanowire/polymer composite comprising first core-shell nanowires and a first polymer, a first insulating layer disposed on the first core-shell nanowire/polymer composite, and a second core-shell nanowire/polymer composite disposed on the first insulating layer and comprising second core-shell nanowires and a second polymer.

The first and second core-shell nanowires may comprise a core comprising a conductive metal and a shell comprising a biocompatible metal. The conductive metal may comprise silver and the biocompatible metal may comprise gold.

The first and second polymers may comprise polymer rubber. The polymer rubber may comprise SBS rubber.

The first and second core-shell nanowire/polymer composites may have a mesh shape.

The stretchable composite may further comprise a second insulating layer disposed under the first core-shell nanowire/polymer composite, and a third insulating layer disposed on the second core-shell nanowire/polymer composite. The first insulating layer, the second insulating layer and the third insulating layer may comprise polymer rubber. The first insulating layer, the second insulating layer and the third insulating layer may have a mesh shape.

The stretchable composite may be used, for example, as a cardiac mesh electrode.

Silver nanowire (Ag NW) is a high conductive material with high aspect ratio, and thus can form a good electrical percolation network. According as Ag NW is encapsulated with Au nanoshell, high conductivity is maintained and Ag ion leaching can be reduced. In addition, the cardiac mesh electrode does not use surfactant degrading the conductivity of Ag NW and can have stable electrical properties under mechanical strain by localization of conducting materials. The core-shell nanowire/polymer composite enables molding and welding process to make large sized device with multi electrode arrays and thus is applicable to large sized heart. The cardiac mesh electrode can perform simultaneous analysis through cardiac mapping and stereotactic pacing effect that offer location-irrelevant pacing, and can be used as a stretchable electrode of biomedical devices for treatment of various cardiac diseases.

For example, Ag@Au NW/SBS composite can be formed as follows.

100 ml of ethylene glycol is pre-heated at 175° C. with 260 rpm stirring. Poly-vinylpirrolidone (PVP, MW 360 k) is dissolved in 30 ml of ethylene glycol and 800 μl of 4 mM copper chloride ($CuCl_2.2H_2O$) solution is added. The solution is injected with 180 ml/hr 10 minutes after silver nitrate ($AgNO_3$) solution with 0.095M concentration and copper solution are injected in ethylene glycol. After the injection was finished, stirring is stopped and the synthesis reaction is performed for 20 minutes to form Ag NW. After the reaction was over, the Ag NW solution is diluted with water (1:4) and is centrifuged at 3000 RPM for 10 minutes. The washing process is repeated 3 times to remove PVP of Ag NW. The washed Ag NW is encapsulated with gold nanoshell to form Ag@Au NW. Ag@Au NWs are dispersed in toluene with 30 mg/ml. The Au@Ag NW solution is mixed with SBS dissolved solution (SBS: toluene is 1:10). The optimized concentration showing highest stretchability is about 45 wt % of Au@Ag nanowires in the Au@Ag NW/SBS composite. The mixed solution is poured in glass mold and dried on hotplates.

FIG. 1 schematically shows a process for forming a gold shell on a silver nanowire without a galvanic reaction according to one embodiment of the present invention.

Referring to FIG. 1, Au is deposited on an Ag NW surface by an epitaxial deposition using a gold sulfite complex such as $Na_3Au(SO_3)_2$. It is very difficult to form Ag@Au NW without galvanic reaction between Ag and Au, and the hollow Au/Ag alloy nanostructure resulted from the galvanic reaction may degrade electrical property and biocompatibility of Ag@Au NW. However, according to embodiments of the present invention, Au nanoshell can be formed on Ag NW while completely inhibiting galvanic replacement reaction by using a sulfite ligand. Au nanoshell can be formed thickly to cover the entire surface of Ag NW.

Sulfite ligand selectively binds to Au cations to lower reduction potential with high stability and prevents any ligand-assisted oxidative etching, and thus sulfite ligand plays very important role in epitaxial deposition of Au on Ag surface.

Since sulfite coordinated Au precursor exhibits high stability, slow injection of Au precursor is not needed, and thus large scale synthesis is possible. Also, by controlling concentration of silver nanowire in the reaction, it is possible to control the thickness of Au shell deposited on Ag surface. The synthesized Ag@Au nanowire (NW) has an average overall diameter of about 180 nm with average Au shell thickness of about 30 nm.

Ag NW has high intrinsic electrical conductivity and good mechanical stretchability, but is limited in biomedical applications due to toxicity resulting from leaching of Ag+ ions. In addition, Gold (Au) has biocompatibility and resistance to oxidation, but is limited in applications to biomedical devices due to its low intrinsic conductivity. However, Ag@Au NW according to embodiments of the present invention is excellent in both electrical conductivity and biocompatibility because Ag NW is encapsulated in a thick shell of Au.

Figure 2:
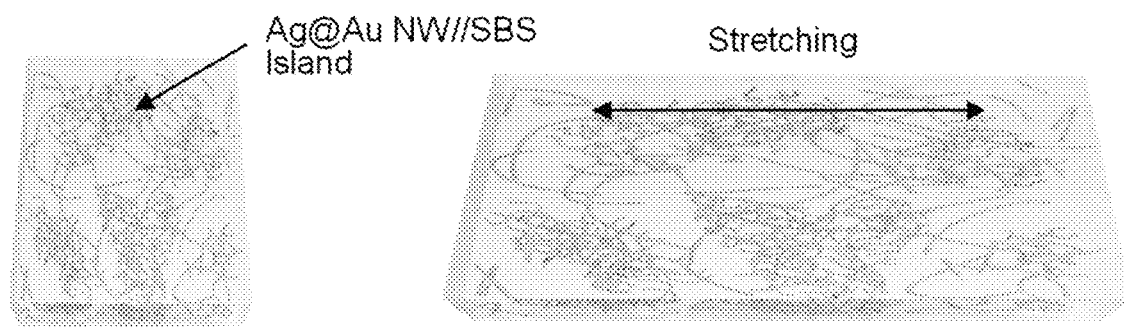
FIG. 2 shows a stretchable conductor consisting of Ag@Au NW/SBS composite according to one embodiment of the present invention.

FIG. 2 shows a stretchable conductor consisting of Ag@Au NW/SBS composite according to one embodiment of the present invention.

Referring to FIG. 2, after exchanging the ligand of the synthesized Ag@Au NW to hexylamine, the Ag@Au NWs are dispersed in toluene and mixed with SBS solution, and the toluene is dried to form Ag@Au NW/SBS composite. The toluene may have more weight than SBS solution (for example, about 10 times). The Ag@Au NW/SBS composite has high electrical conductivity, biocompatibility and stretchability.

Figure 3:
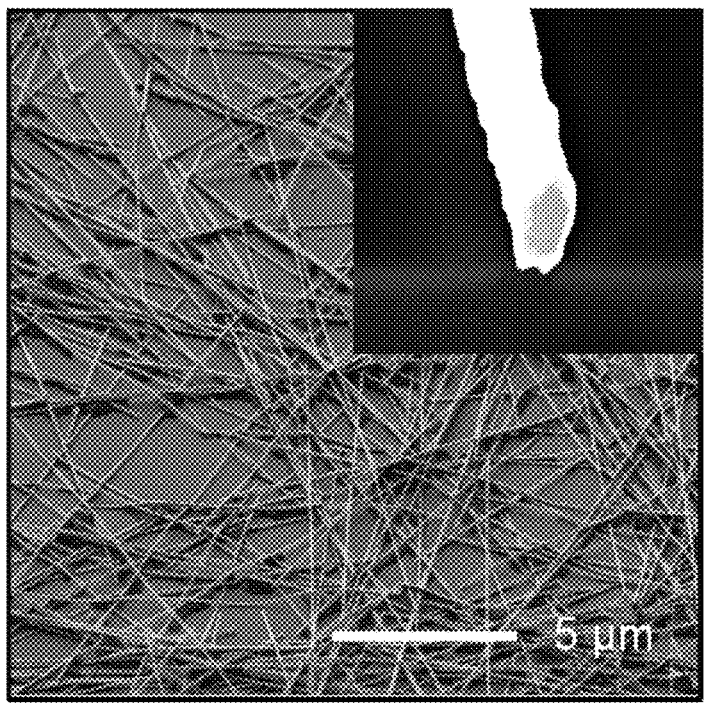
FIG. 3 shows a SEM image of Ag@Au NW according to one embodiment of the present invention.

FIG. 3 shows an SEM image of Ag@Au NW according to one embodiment of the present invention.

Referring to FIG. 3, the SEM image shows Ag@Au NW and the inset shows clear contrast between Ag NW core and Au shell as a backscatter image.

Figure 4:
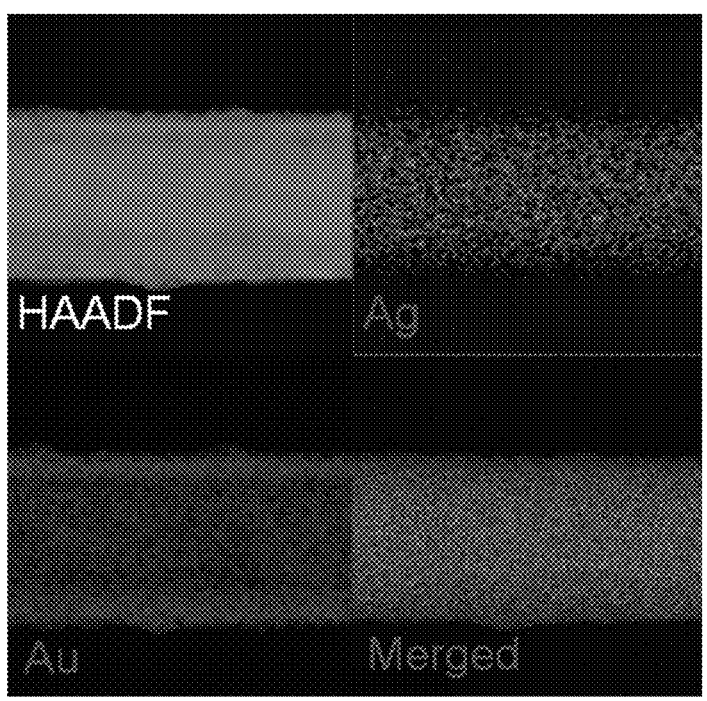
FIG. 4 shows EDS mapping for identifying a core-shell structure of Ag@Au NW according to one embodiment of the present invention.

FIG. 4 shows EDS mapping for identifying a core-shell structure of Ag@Au NW according to one embodiment of the present invention.

Referring to FIG. 4, EDS (Energy-dispersive X-ray spectroscopy) mapping shows a signal of Ag, Au elements which confirm the core shell structure of Ag@Au NW. Galvanic substitution reaction is inhibited so that etching of Ag NW or formation of hollow structure is not observed.

Figure 5:
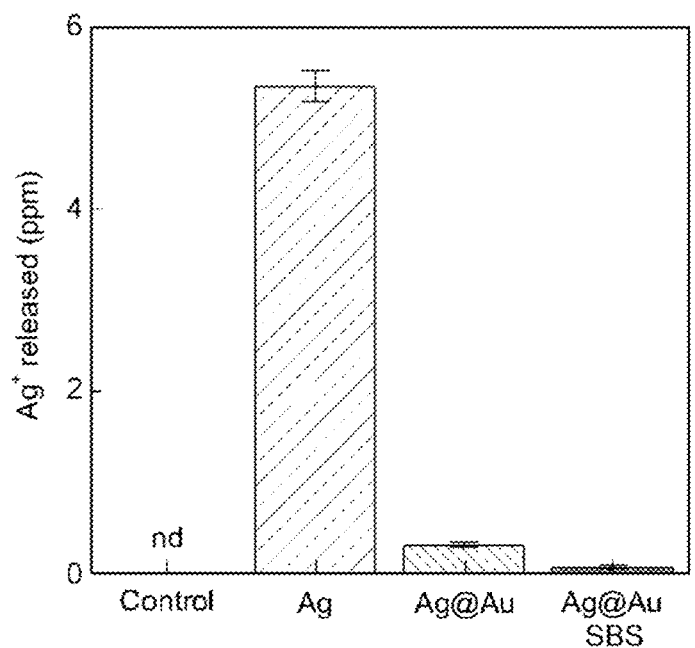
FIG. 5 shows ICP-MS (Inductively coupled plasma mass spectroscopy) data for analyzing Ag ion leaching from Ag NW, Ag@Au NW and Ag@Au NW/SBS composite.

FIG. 5 shows ICP-MS (Inductively coupled plasma mass spectroscopy) data for analyzing Ag ion leaching from Ag NW, Ag@Au NW and Ag@Au NW/SBS composite. Ag NW, Ag@Au NW and Ag@Au NW/SBS composites are dispersed in DMEM (Dulbecco Modified Eagle's Medium) solution for 3 days in cell incubator and the amount of Ag+ ions leached is analyzed by inductively coupled plasma mass spectroscopy.

Referring to FIG. 5, Au shell effectively prevents Ag ions from leaching. In comparison with Ag+ ion leaching of Ag NW, Ag+ ion leaching is decreased to 5.8% in Ag@Au NW and decreased to 1.2% in Ag@Au NW/SBS composite.

Figure 6:
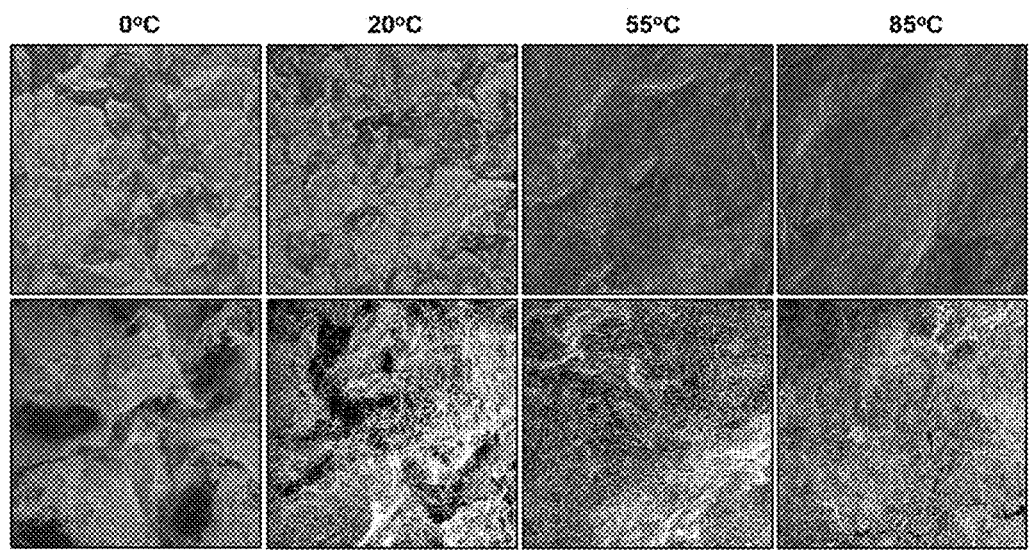
FIG. 6 shows SEM images of Ag@Au NW/SBS composite depending on fabrication processing temperatures.
Figure 7:
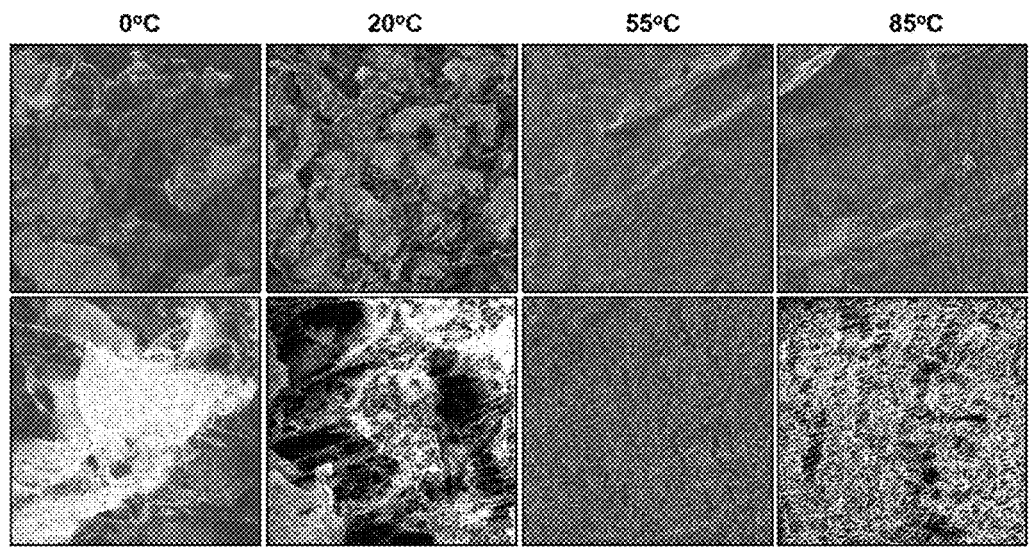
FIG. 7 shows SEM images of the Ag@Au NW/SBS composite of FIG. 6 when stretched under 30% strain.

FIG. 6 shows SEM images of Ag@Au NW/SBS composite depending on fabrication processing temperatures, and FIG. 7 shows SEM images of the Ag@Au NW/SBS composite of FIG. 6 when stretched under 30% strain.

Referring to FIGS. 6 and 7, Ag@Au NW/SBS composite has good biocompatibility, and shows high stretchabiltiy and stable electrical performance. During the drying process of the solution, Ag@Au NW shows clustering effect of densifying electron pathway even under mechanical deformation. The mixture of Ag@Au NWs and SBS in toluene with an appropriated concentration is poured on the glass mold. Drying at low temperature (room temperature; 20° C.) maximizes the clustering effect by lengthening the drying time for two days. The SEM image shows clustering island mostly composed of Ag@Au NW. While stretching, most strain is applied between clustering regions that is mainly coupled with SBS to form SBS bridges (FIG. 7). However, the electrical conductivity is still maintained by ultra-long Ag@Au NW percolation structure on the SBS bridges. Ag@Au NW/SBS composite shows homogeneous distribution of Ag@Au NW when dried under 55° C. and 85° C., and clustering island and SBS bridges are not shown.

Figure 8:
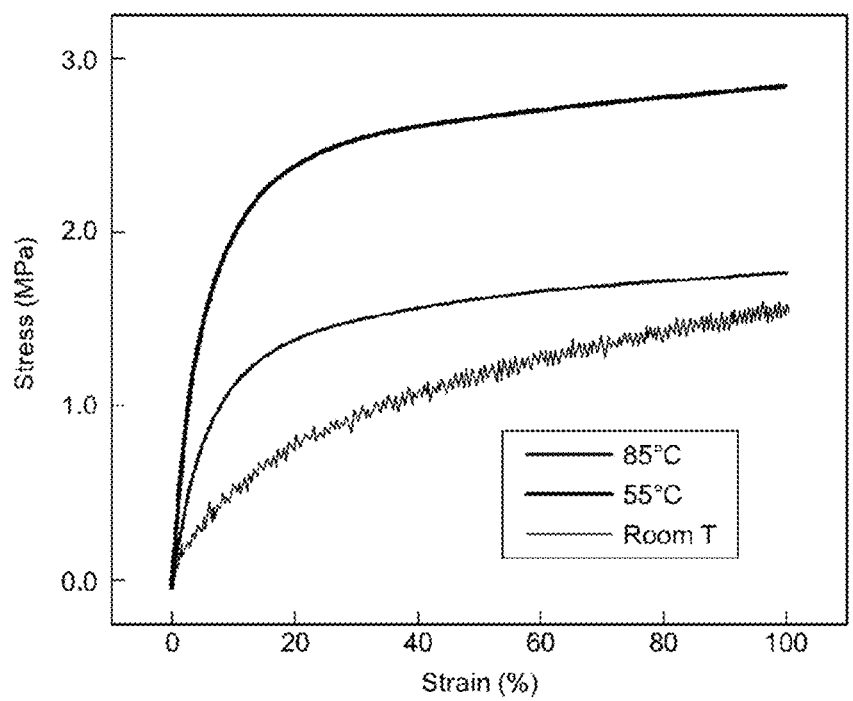
FIG. 8 shows strain-stress curves of Ag@Au NW/SBS composite depending on fabrication processing temperatures.

FIG. 8 shows strain-stress curves of Ag@Au NW/SBS composite depending on fabrication processing temperatures.

Referring to FIG. 8, Ag@Au NW/SBS composite shows stiff strain-stress curve. However, SBS bridge structure where reinforced stiff island region is covered by absorbing applied strain, results in low modulus of Ag@Au NW/SBS composite.

Figure 9:
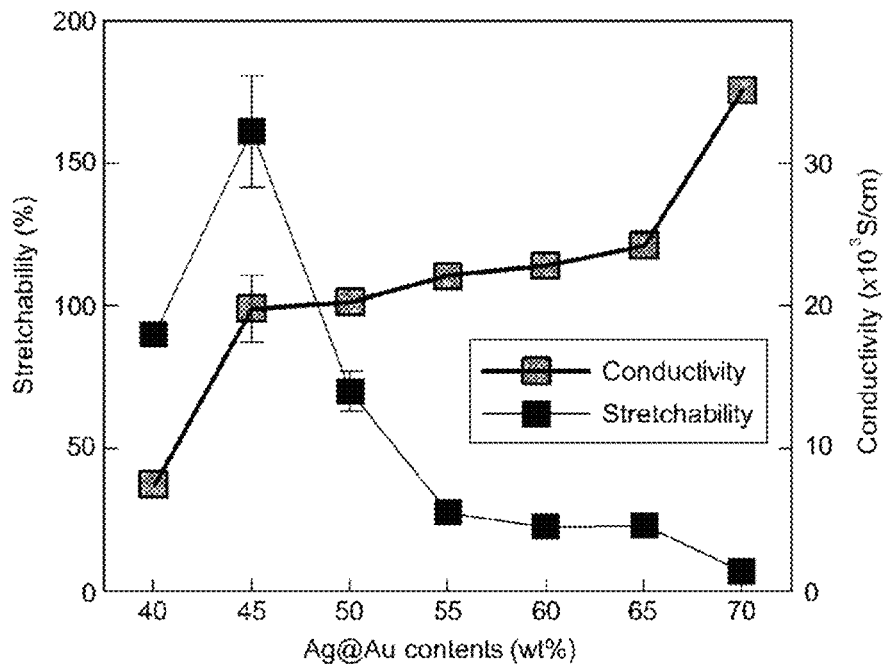
FIG. 9 shows stretchability and conductivity of Ag@Au NW/SBS composite depending on Ag@Au NW contents.

FIG. 9 shows stretchability and conductivity of Ag@Au NW/SBS composite depending on Ag@Au NW contents.

Referring to FIG. 9, the conductivity shows escalating tendency in correspondence of increase in contents of the Ag@Au NWs, and Ag@Au NW/SBS composite has maximum conductivity of 35,000 S/cm when the content of the Ag@Au NWs is 70 wt %. In addition, Ag@Au NW/SBS composite has maximum stretchability of 180% when the content of the Ag@Au NWs is 45 wt %, and this implies threshold contents of SBS required to form SBS bridges having still high conductivity of 19,783 S/cm.

Figure 10:
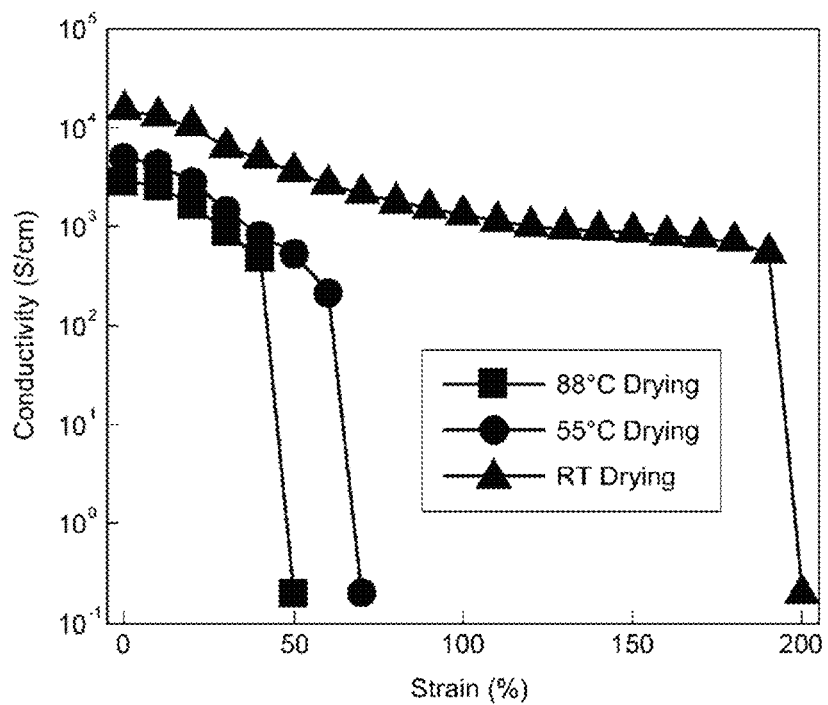
FIG. 10 shows conductivity change when Ag@Au NW/SBS composite is mechanically stretched.

FIG. 10 shows conductivity change when Ag@Au NW/SBS composite is mechanically stretched.

Referring to FIG. 10, with drying process of 20° C. (RT Drying), the high densified Ag@Au NW clustering region and percolated conductive network on the SBS bridge shows stable performance of conductivity while stretched up to 180%.

Figure 11:
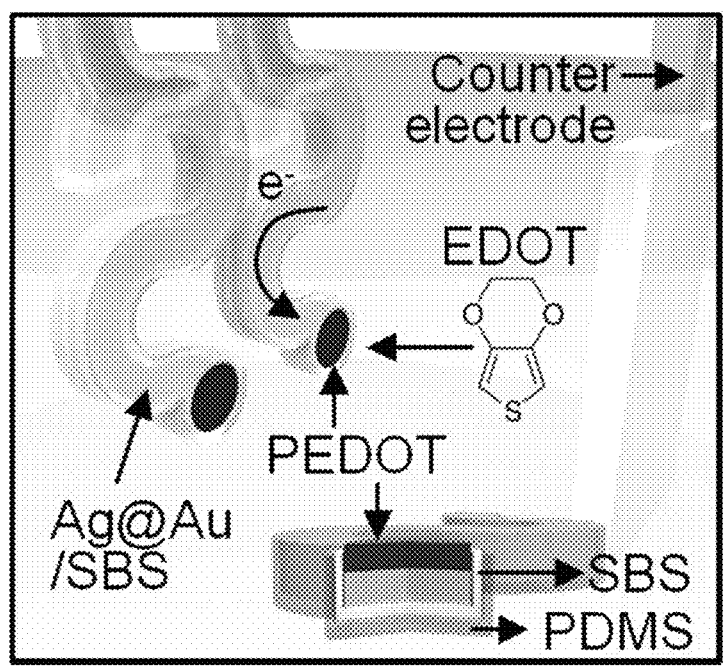
FIG. 11 schematically shows an electrodeposition process of PEDOT on an Ag@Au NW/SBS electrode.

FIG. 11 schematically shows an electrodeposition process of PEDOT on an Ag@Au NW/SBS electrode.

Referring to FIG. 11, in order to exploit the Au@Ag NW/SBS composite as a epicardial electrode, PEDOT (Poly (3,4-ethylenedioxythiophene)) is deposited on the surface of an electrode to increase charge injection, and thus impedance can be lowered. PEDOT can be formed by electropolymerization of 3,4-EDOT (Ethylenedioxythiophene). For example, PEDOT can be deposited on the surface of the electrode by dissolving 0.01M of 3,4-EDOT (Ethylenedioxythiophene) and 0.01M of Lithium perchlorate ($LiClO_4$) in acetonitrile, dipping the fabricated mesh electrode into the solution, and performing galvanostatic electrodepostion under 0.1 mA of current using 2-electrode system (potential vs. Ag/AgCl reference electrode) for 1000 seconds.

Au@Ag NW/SBS composite and SBS are patterned in a mold of serpentine shape, and Au@Ag NW/SBS composite whose electrode areas are not covered is sandwiched by SBS layer. For insulation purpose, the electrode line may be encapsulated with silicone rubber.

Figure 12:
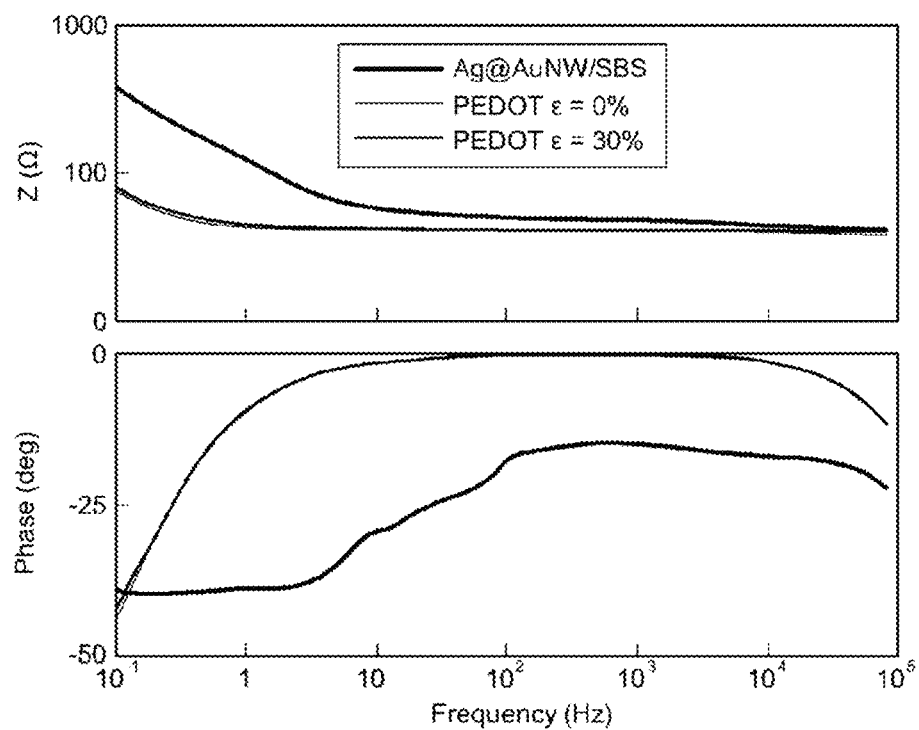
FIG. 12 shows impedance and phase of Ag@Au NW/SBS electrode and stretched Ag@Au NW/SBS electrode before and after PEDOT deposition.

FIG. 12 shows impedance and phase of Ag@Au NW/SBS electrode and stretched Ag@Au NW/SBS electrode before and after PEDOT deposition.

Referring to FIG. 12, the impedance of the epicardial electrode is reduced after the electrodeposition of PEDOT. Even though the epicardial electrode is stretched up to 30%, the electrochemical property is maintained.

Figure 13:
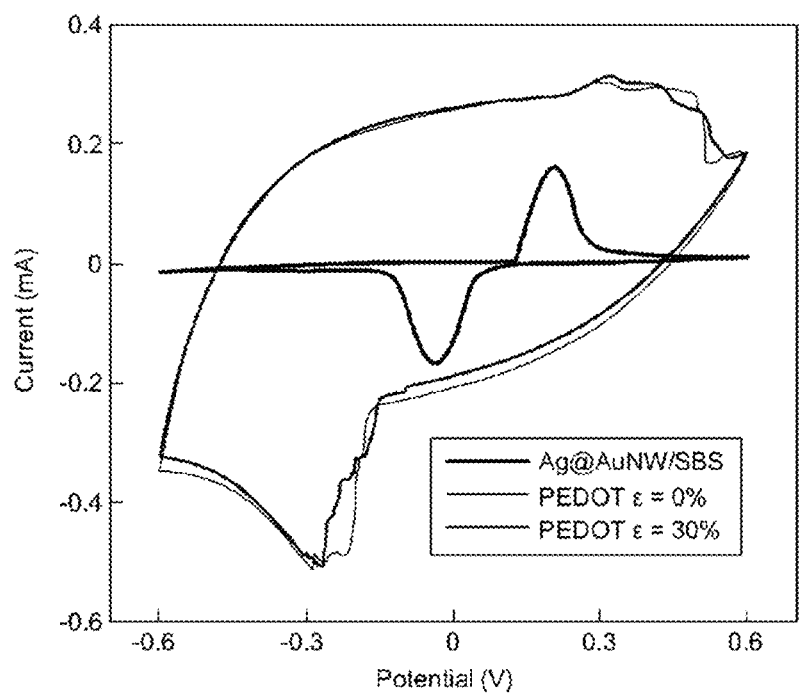
FIG. 13 shows cyclic voltammetry of Ag@Au NW/SBS electrode and stretched Ag@Au NW/SBS electrode before and after PEDOT deposition.

FIG. 13 shows cyclic voltammetry of Ag@Au NW/SBS electrode and stretched Ag@Au NW/SBS electrode before and after PEDOT deposition.

Referring to FIG. 13, in cyclic voltammogram, cathodal charge storage capacity is increased from 12.98 $mC/cm^2$ to 80.11 $mC/cm^2$ after the electrodeposition of PEDOT, and the CV curve is maintained even though it is stretched by 30%.

Figure 14:
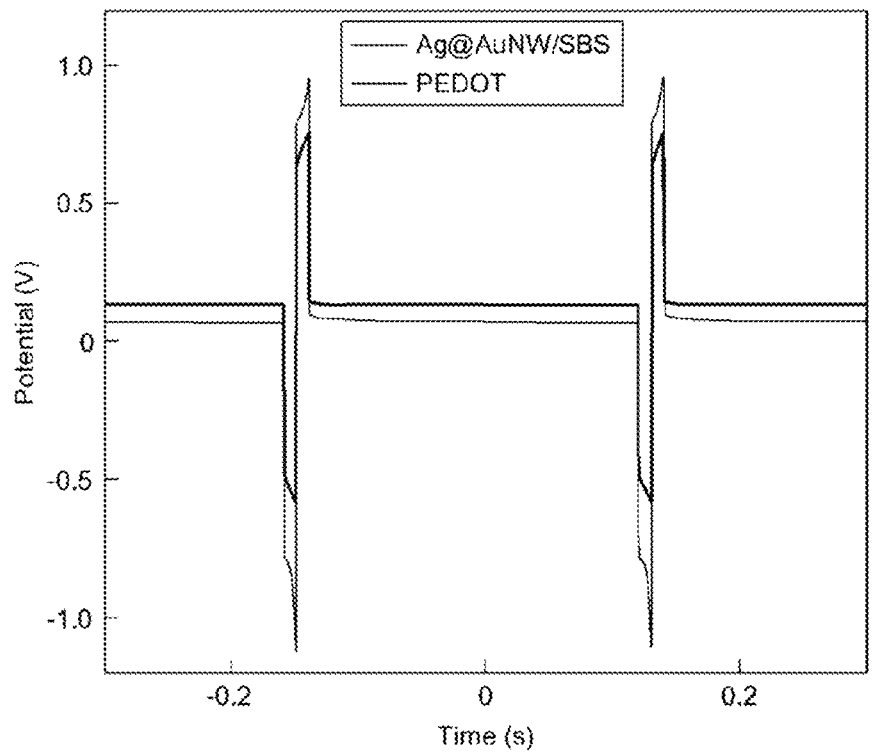
FIG. 14 shows charge injection under 2 mA biphasic current stimulation on Ag@Au NW/SBS electrode before and after PEDOT deposition.

FIG. 14 shows charge injection under 2 mA biphasic current stimulation on Ag@Au NW/SBS electrode before and after PEDOT deposition.

Referring to FIG. 14, the amount of charge injection is the same with less potential applied at the PEDOT coated epicardial electrode under condition of 2 mA biphasic current during 20 ms. The epicardial electrode has good electrochemical properties as well as high conductivity by intrinsic materials, and can accurately measure signals from the heart.

Figure 15:
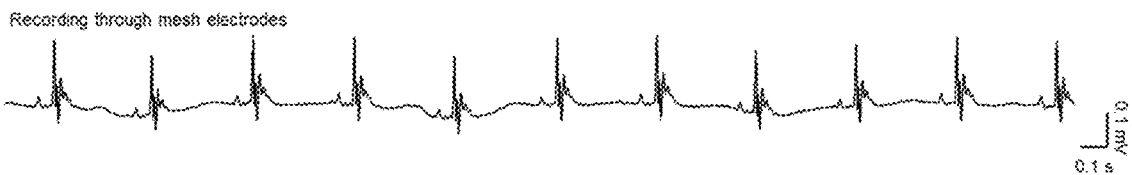
FIG. 15 shows intracardiac electrogram recorded from Ag@Au NW/SBS electrode coated by PEDOT in a rat heart.
Figure 16:
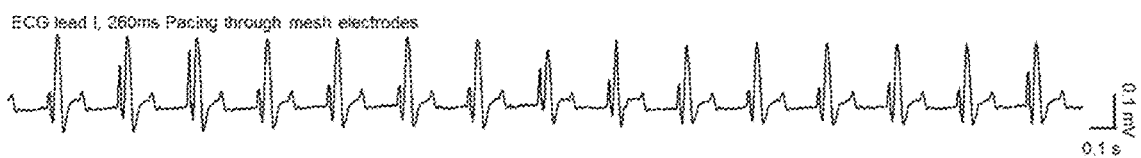
FIG. 16 shows surface ECG (lead 1) of a rat heart while conducting pacing (260 cycle length) with Ag@Au NW/SBS electrode coated by PEDOT.

FIG. 15 shows intracardiac electrogram recorded from Ag@Au NW/SBS electrode coated by PEDOT in a rat heart, and FIG. 16 shows surface ECG (lead 1) of a rat heart while conducting pacing (260 cycle length) with Ag@Au NW/SBS electrode coated by PEDOT.

Referring to FIGS. 15 and 16, the intracardial signal from the epicardial surface can be measured from a pair of electrodes, and the heart rate can be accelerated by the pacing rate when the electrical stimulation is applied with 260 ms of cycle length.

Figure 17:
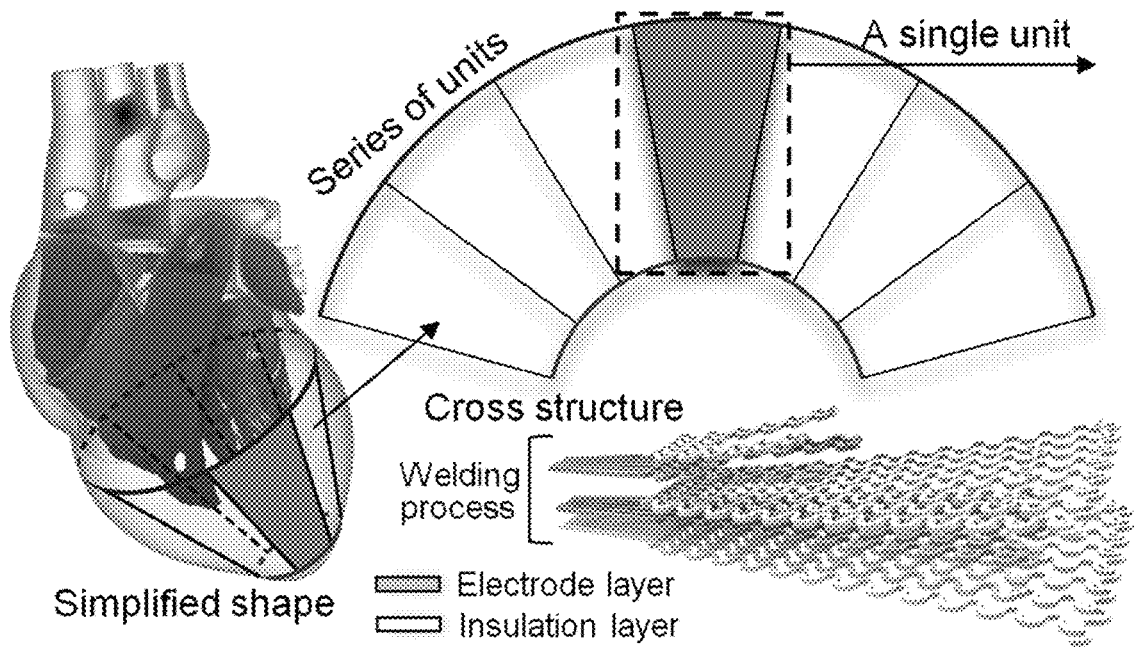
FIG. 17 shows a design of a cardiac mesh electrode according to one embodiment of the present invention.

FIG. 17 shows a design of a cardiac mesh electrode according to one embodiment of the present invention.

Referring to FIG. 17, the cardiac mesh electrode may comprise a plurality of unit mesh electrodes, and the unit mesh electrode may comprise a plurality of line electrodes. For example, the cardiac mesh electrode may include seven unit mesh electrodes, and the unit mesh electrode may include six pairs of line electrodes. With respect to one pair of line electrodes, one line electrode may be disposed on a SBS layer and the other may be disposed under the SBS layer with the SBS layer interposed therebetween. The line electrode has a serpentine shape. SBS meshes and Au@Ag NW/SBS composite are stacked and a single unit mesh electrode consisting of six pairs of electrodes is formed through welding process. Due to the thermoplastic property of SBS rubber, the SBS mesh and SBS in the Au@Ag NW/SBS composite can be diffused and welded under heat and pressure. A plurality of unit mesh electrodes are arrayed and welded to each other, and thus the cardiac mesh electrode is formed. In order to firmly encapsulate side of the conducting layer, silicon rubber is coated except opened electrode zone. In order to surround the heart, the cardiac mesh electrode may have a shape (a fan shape) in which a plurality of unit mesh electrodes are combined to be spread.

Figure 18:
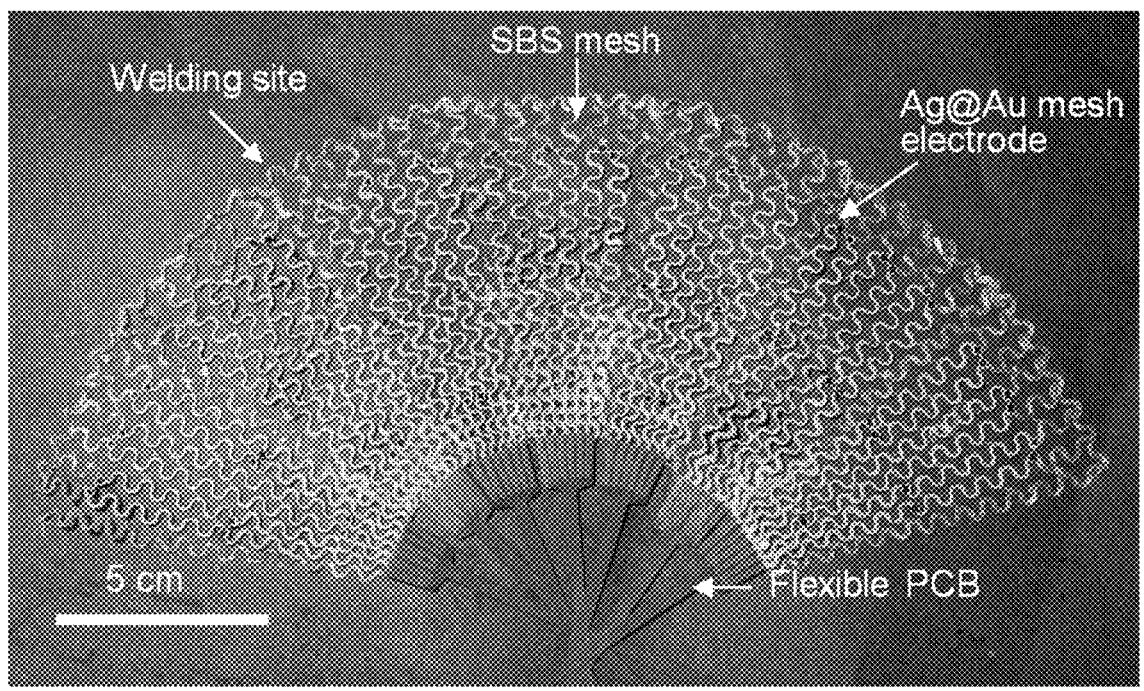
FIG. 18 shows a spread cardiac mesh electrode connected to flexible PCB.
Figure 19:
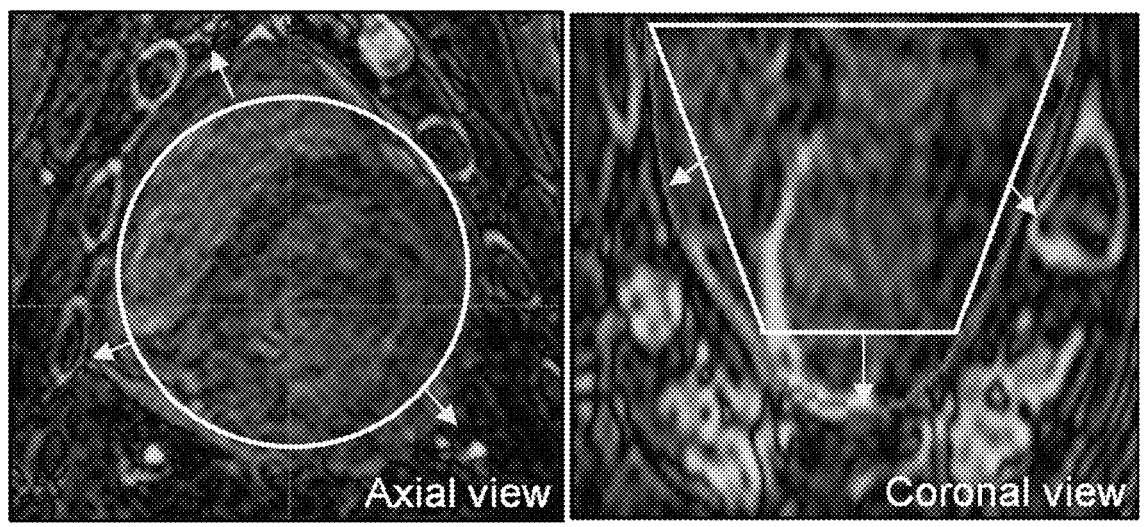
FIG. 19 shows a MRI image of a live swine heart.

FIG. 18 shows a spread cardiac mesh electrode connected to flexible PCB, and FIG. 19 shows a MRI image of a live swine heart.

Referring to FIGS. 18 and 19, the cardiac mesh electrode fitting the shape and size of the heart can be prepared based on the MRI cardiac image. The block copolymer structure of SBS rubber has shape memory effect as the polymer has soft segment for switching and hard segment for cross-links. Therefore, the block copolymer of SBS rubber has deformation in the polymer chain at a temperature above the glass transition temperature so that it is deformed and conform to the size of the heart. At this state, if the temperature is lowered below the glass transition temperature, the shape can be fixed.

Figure 20:
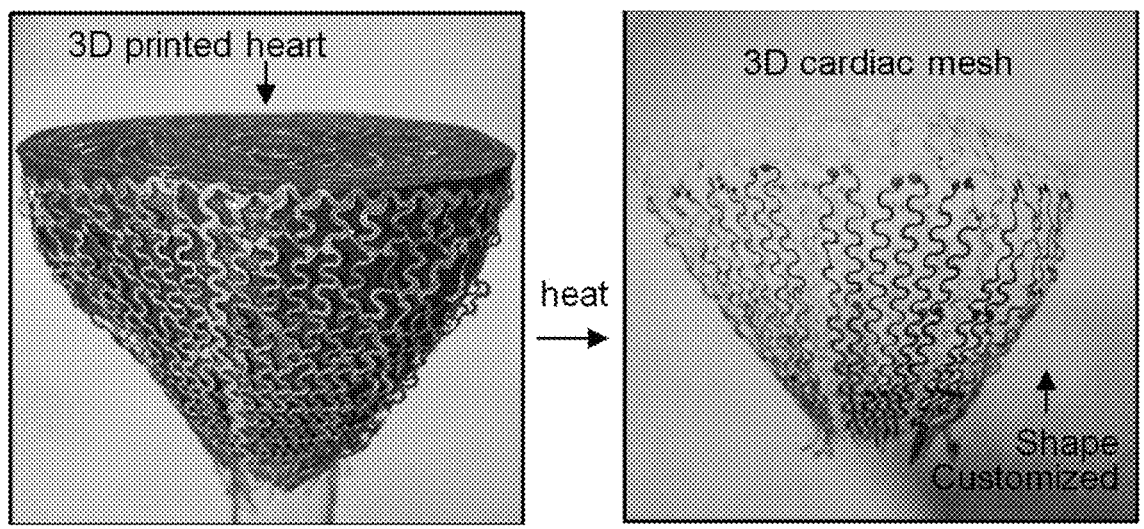
FIG. 20 shows a cardiac mesh electrode and a process of customizing the cardiac mesh electrode.

FIG. 20 shows a cardiac mesh electrode and a process of customizing the heart mesh electrode.

Referring to FIG. 20, the cardiac mesh electrode can maintain the shape of the heart by heating and cooling process using 3D printed heart model.

Figure 21:
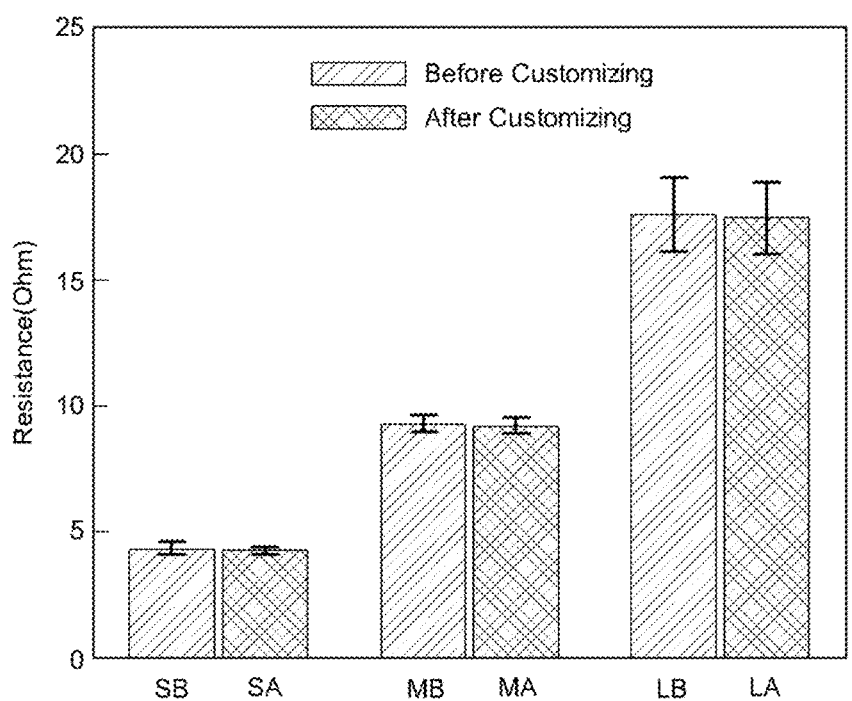
FIG. 21 shows the resistance of cardiac mesh electrode lines before and after a customizing process.

FIG. 21 shows the resistance of cardiac mesh electrode lines before and after a customizing process.

Referring to FIG. 21, even though the cardiac mesh electrode stretches to the original size of the heart, the resistance of the electrode barely changes after the customization process.

Figure 22:
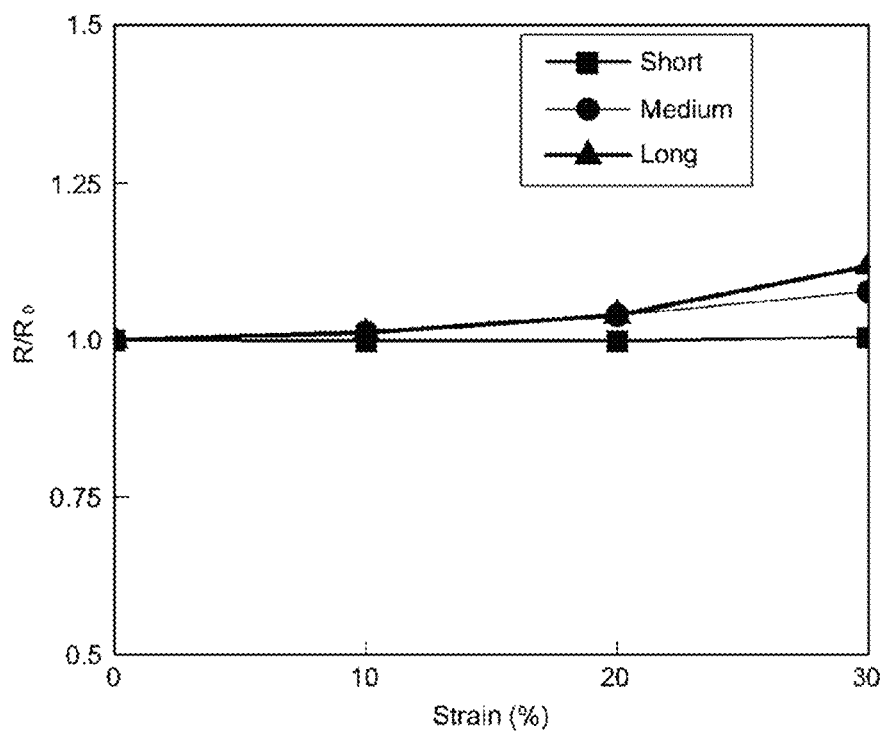
FIG. 22 shows the resistance change of a cardiac mesh electrode under strain.
Figure 23:
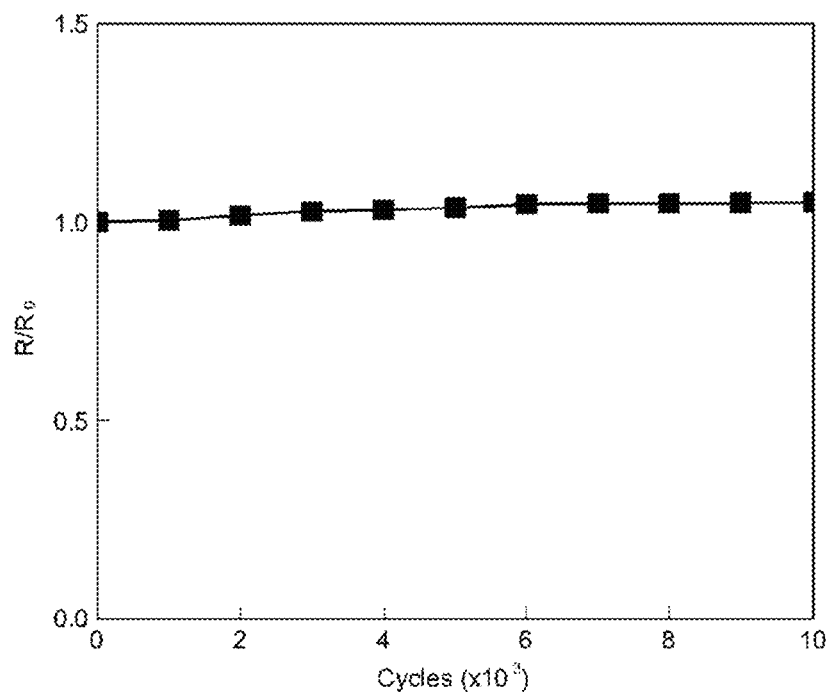
FIG. 23 shows the cyclic test result of a cardiac mesh electrode under 30% strain.

FIG. 22 shows the resistance change of a cardiac mesh electrode under strain, and FIG. 23 shows the cyclic test result of a cardiac mesh electrode under 30% strain. Each resistance of electrode line are measured under 30% strain which occurs from the circumferential strain during systole and diastole cycles, and the resistance change of the middle sized electrode lines are measured during cyclic strain test. Referring to FIGS. 22 and 23, the cardiac mesh electrode enables to measure heart signals and stimulate the heart even under mechanical and cyclic strains.

Figure 24:
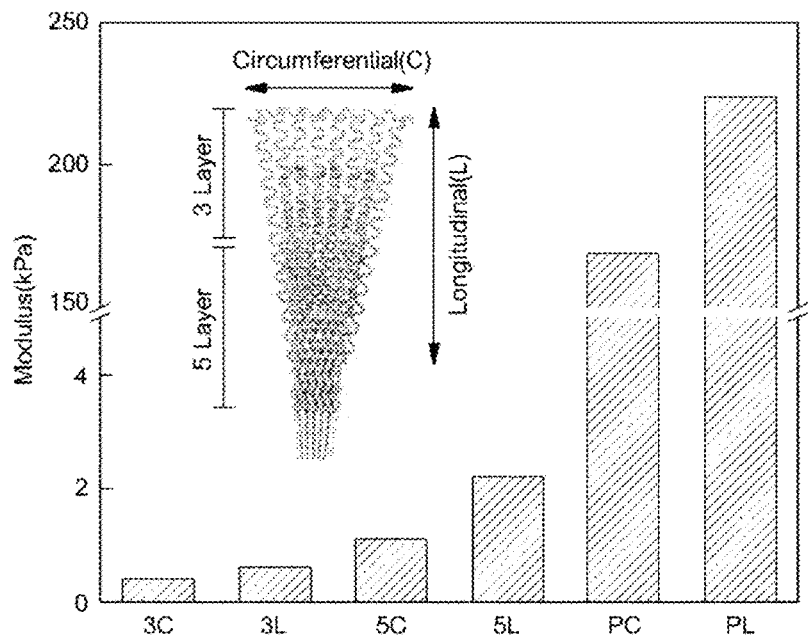
FIG. 24 shows a comparison of modulus of a cardiac mesh electrode depending on a layer section of the cardiac mesh electrode and modulus of a swine heart.

FIG. 24 shows a comparison of modulus of a cardiac mesh electrode depending on a layer section of the cardiac mesh electrode and modulus of a swine heart. (PC: Porcine circumferential direction; PL: Porcine longitudinal direction)

Referring to FIG. 24, since the modulus of the cardiac mesh electrode is much lower than the modulus of the porcine heart (myocardium), the cardiac mesh electrode does not inhibit the pumping activity of the heart, and does not impede the movement of ventricles and left ventricle (LV) pressure.

Figure 25:
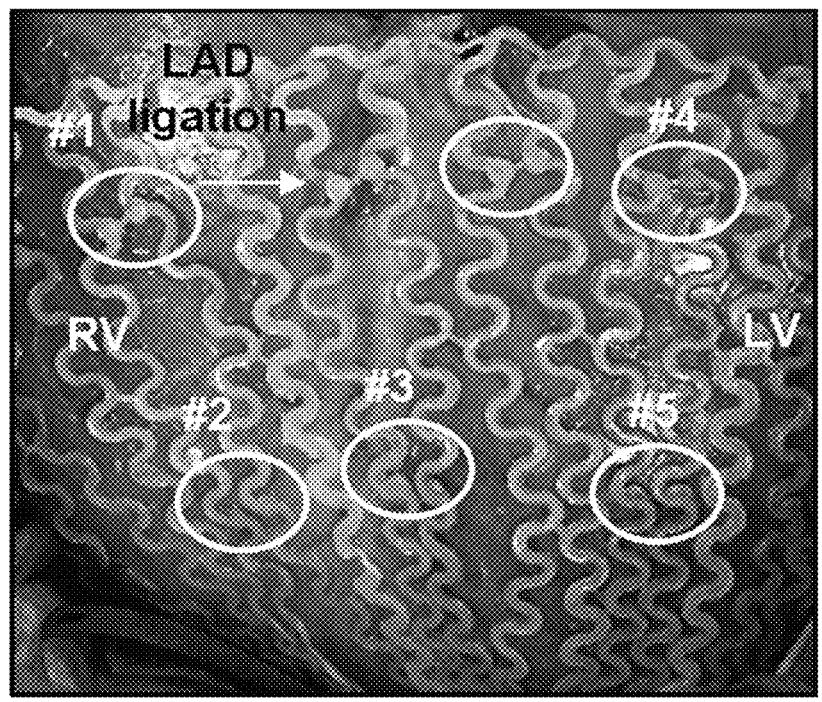
FIG. 25 shows an image of a cardiac mesh electrode implanted in a swine heart with LAD (left anterior descending coronary artery) occluded.
Figure 26:
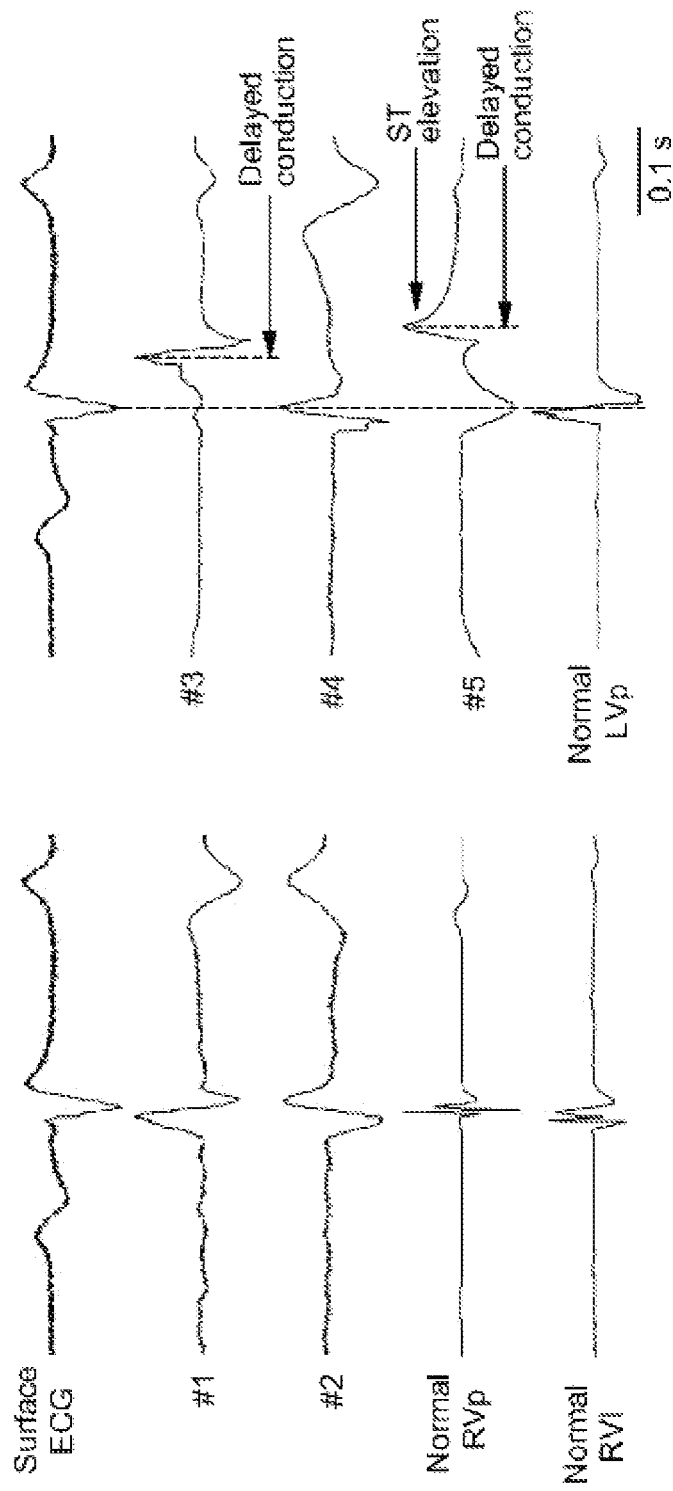
FIG. 26 shows intracardiac electrogram of a cardiac mesh electrode 1 hour after LAD occlusion.

FIG. 25 shows an image of a cardiac mesh electrode implanted in a swine heart with LAD (left anterior descending coronary artery) occluded, and FIG. 26 shows intracardiac electrogram of a heart mesh electrode 1 hour after LAD occlusion.

Referring to FIG. 25, before the implantation of the cardiac mesh, left anterior descending coronary artery (LAD) is occluded with balloon catheter in swine heart to induce acute myocardial infarction.

Referring to FIG. 26, intracardiac electrogram is measured simultaneously at each position one hour after LAD occlusion. Due to the LAD occlusion, wide QRS duration informs that myocardial tissues are damaged at left ventricles anterior (LVa) in comparison with normal position. Especially at the position of number 3 to number 5, delayed conduction and ST elevation resulting from myocardial injuries are shown.

Figure 27:
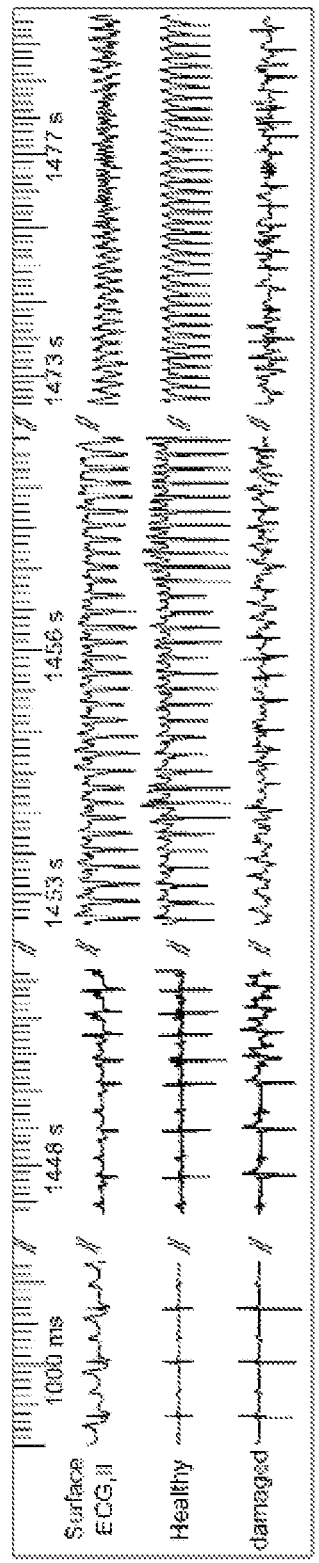
FIG. 27 shows intracardiac electrogram of surface ECG, healthy tissue and damaged tissue.

FIG. 27 shows intracardiac electrogram of surface ECG, healthy tissue and damaged tissue.

Referring to FIG. 27, as myocardial infarction becomes more severe, cardiac function worsens so that ventricular tachycardia (VT) meaning rapid heartbeat and ventricular fibrillation (VF) meaning disordered heartbeat are induced. At the onset of VT, signals from the normal tissue show regular and fast heartbeat, but signals from damaged tissue show disordered pattern.

Figure 28:
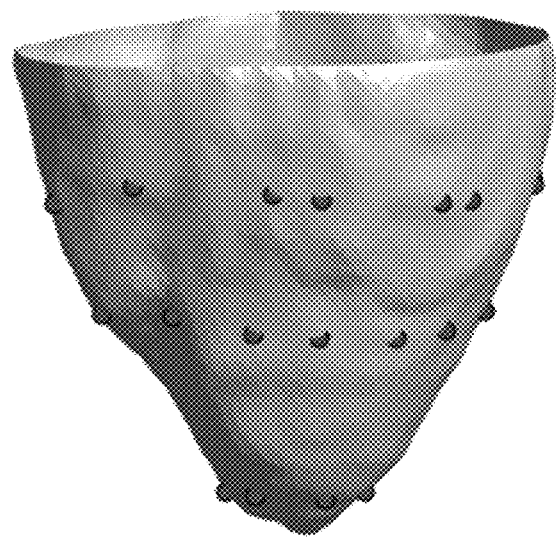
FIG. 28 shows bipolar electrode configuration by the 3D reconstructed image from MRI.
Figure 29:
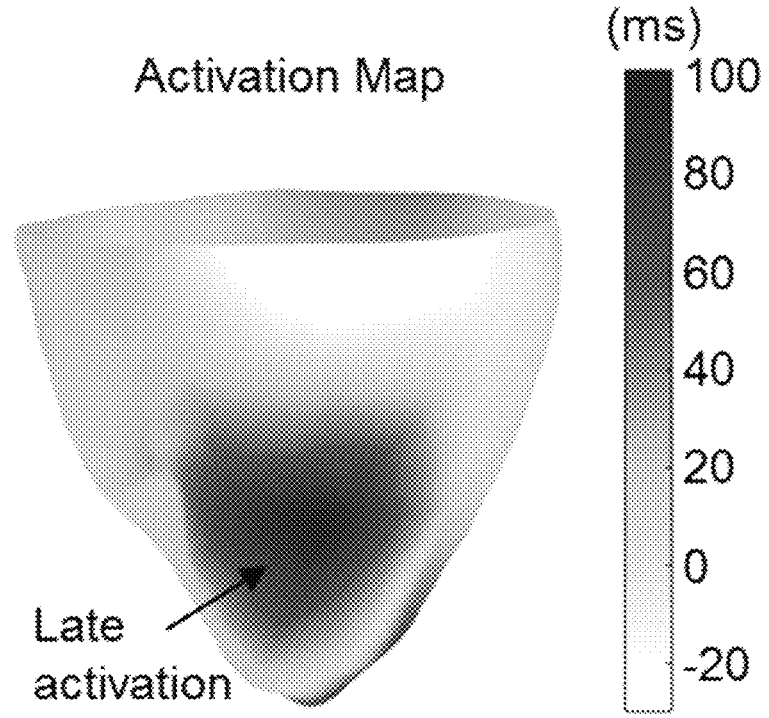
FIG. 29 shows an activation map of 3D model and FIG. 30 shows a voltage map of 3D model.
Figure 30:
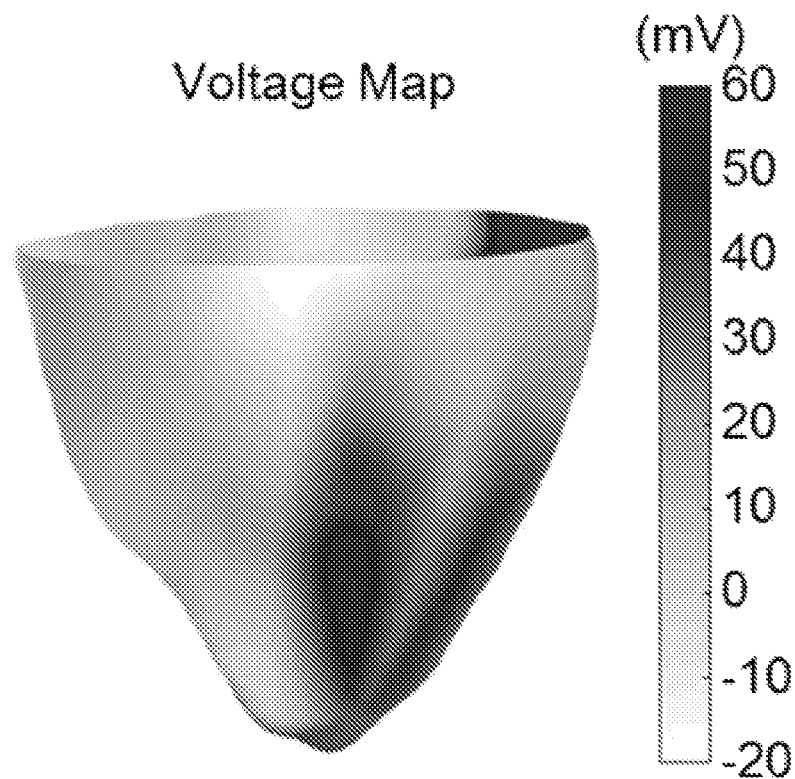

FIG. 28 shows bipolar electrode configuration by the 3D reconstructed image from MRI, FIG. 29 shows an activation map of 3D model and FIG. 30 shows a voltage map of 3D model.

Referring to FIGS. 28 to 30, local electrical activity is recorded from 24 pairs of electrodes on the epicardium and an activation map is constructed by recorded bipolar intracardial electrogram which shows the time difference of the maximum slope of the voltage based on the surface ECG (lead II) after interpolation. From the isochronal cardiac activation mapping, the damaged heart muscle can be detected and it corresponds to voltage map which is the map of difference of highest and lowest voltage.

Figure 31:
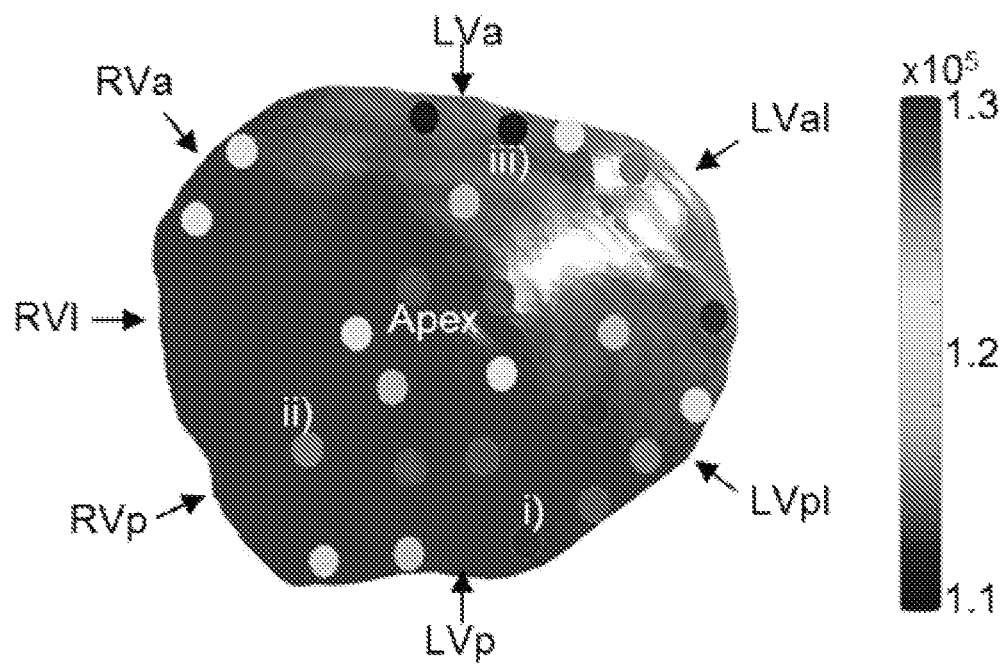
FIG. 31 shows contractility under 3D coordinated electrical stimulation.
Figure 32:
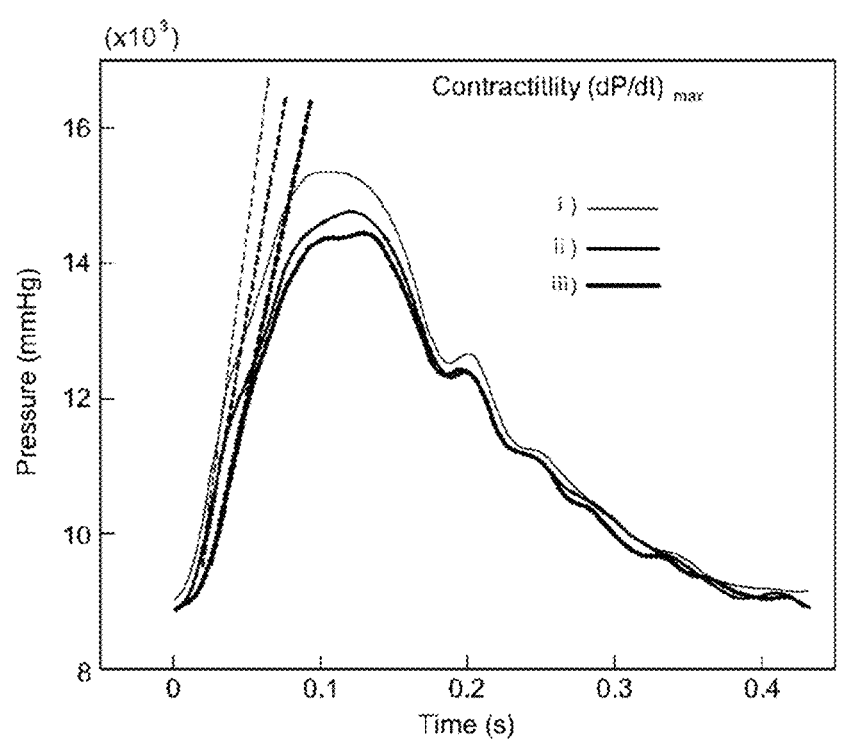
FIG. 32 shows a single pressure curve by stereotactic pacing.

FIG. 31 shows contractility under 3D coordinated electrical stimulation, and FIG. 32 shows a single pressure curve by stereotactic pacing.

Referring to FIGS. 31 and 32, average contractility (dP/dtmax) is calculated under 3D coordinated electrical stimulation based on the pressure curve while pacing is simultaneously occurred, and pacing along the lateral side of the left ventricle is relatively effective to restore cardiac function.

As above explained, chest stereotactical pacing using a cardiac mesh electrode according to embodiments of the present invention is applicable to cardiac synchronization therapy for patients who are ineffective by the existing cardiac pacing catheter method.

As above, the exemplary embodiments of the present invention have been described. Those skilled in the art will appreciate that the present invention may be embodied in other specific ways without changing the technical spirit or essential features thereof. Therefore, the embodiments disclosed herein are not restrictive but are illustrative. The scope of the present invention is given by the claims, rather than the specification, and also contains all modifications within the meaning and range equivalent to the claims.

INDUSTRIAL APPLICABILITY

A core-shell nanowire according to embodiments of the present invention can have good biocompatibility. The stretchable composite comprising the core-shell nanowire can have high conductivity and good biocompatibility. The stretchable composite can be used in various fields such as a medical device and the like.

The invention claimed is:

1. A stretchable composite comprising:
a first core-shell nanowire/polymer composite comprising first core-shell nanowires dispersed in a first polymer;
a first insulating layer disposed on the first core-shell nanowire/polymer composite; and
a second core-shell nanowire/polymer composite disposed on the first insulating layer and comprising second core-shell nanowires dispersed in a second polymer,
wherein each of the first core-shell nanowires comprises a first core comprising a conductive metal and a first shell formed on the first core and comprising a biocompatible metal,
wherein each of the second core-shell nanowires comprises a second core comprising a conductive metal and a second shell formed on the second core and comprising a biocompatible metal,
and
wherein the first core-shell nanowire/polymer composite, the first insulating layer, and the second core-shell nanowire/polymer composite each have a mesh shape.

2. The stretchable composite of claim 1, wherein the first core and the second core comprise silver and the first shell and the second shell comprise gold.

3. The stretchable composite of claim 1, wherein the first polymer and the second polymer comprise polymer rubber.

4. The stretchable composite of claim 3, wherein the polymer rubber comprises SBS rubber.

5. The stretchable composite of claim 1, further comprising a second insulating layer disposed under the first core-shell nanowire/polymer composite and a third insulating layer disposed on the second core-shell nanowire/polymer composite,
wherein the first insulating layer, the second insulating layer and the third insulating layer each comprise polymer rubber, and
wherein the second insulating layer and the third insulating layer each have a mesh shape.

6. The stretchable composite of claim 1, wherein the first core-shell nanowire/polymer composite is a first electrode layer including a first plurality of line electrodes, each of the first plurality of line electrodes being disposed under the first insulating layer and having a serpentine shape, and the second core-shell nanowire/polymer composite is a second electrode layer including a second plurality of line electrodes, each of the second plurality of line electrodes being disposed over the first insulating layer and having a serpentine shape.

* * * * *